US007683019B2

(12) United States Patent
da Silva et al.

(10) Patent No.: US 7,683,019 B2
(45) Date of Patent: Mar. 23, 2010

(54) EXTRUDED ARTISAN SOAP HAVING INNER VEIN

(75) Inventors: Pedro Marques da Silva, Sao Paulo (BR); Katia Cristina Baquete, Sao Paulo (BR)

(73) Assignee: Conopco, Inc., Englewood Cliffs, NJ (US)

( * ) Notice: Subject to any disclaimer, the term of this patent is extended or adjusted under 35 U.S.C. 154(b) by 621 days.

(21) Appl. No.: 11/680,800

(22) Filed: Mar. 1, 2007

(65) Prior Publication Data

US 2008/0214430 A1 Sep. 4, 2008

(51) Int. Cl.
*A61K 7/00* (2006.01)

(52) U.S. Cl. ....................... 510/141; 510/146; 510/152; 510/447; 510/451

(58) Field of Classification Search ....................... None
See application file for complete search history.

(56) References Cited

U.S. PATENT DOCUMENTS 3,294,692 A * 12/1966 Kelly et al. ................. 510/146
3,663,671 A 5/1972 Meye et al.
3,673,294 A 6/1972 Matthaei
3,676,538 A 7/1972 Patterson
3,723,325 A 3/1973 Parran, Jr.
3,832,431 A 8/1974 Matthaei
3,884,605 A 5/1975 Grelon
3,940,220 A 2/1976 D'Arcangeli
3,993,722 A 11/1976 Borcher et al.
4,304,745 A 12/1981 Alderson et al.
4,310,479 A 1/1982 Ooms et al.
4,474,545 A 10/1984 Mazzoni
4,695,395 A 9/1987 Caswell et al.
4,720,365 A 1/1988 Schonig et al.
6,383,999 B1 5/2002 Coyle et al.
6,390,797 B1 5/2002 Myers
6,730,642 B1 5/2004 Aronson et al.
2003/0171232 A1 9/2003 Freeman et al.

FOREIGN PATENT DOCUMENTS

DE 1 924 980 5/1969
WO 01/91990 A1 12/2001

OTHER PUBLICATIONS

International Search Report PCT/EP/2008/050432 Aug. 29, 2008.

* cited by examiner

*Primary Examiner*—Necholus Ogden, Jr.
(74) *Attorney, Agent, or Firm*—Michael P. Aronson

(57) ABSTRACT

An extruded and stamped personal washing bar comprising an artisan crafted appearance having top and bottom stamped faces bounded by a parting line or edge band and a horizontal plane intersecting the parting line or edge band, said bar further comprising an outer surfactant phase and a substantially contiguous inner vein comprising a thermoplastic mass, wherein said inner vein is located between the top and bottom stamped faces of the bar and wherein a projection of the inner vein onto the horizontal plane intersecting the parting line or edge band has a maximum width that is at least 20% of a maximum width of the bar in said horizontal plane.

7 Claims, 5 Drawing Sheets

EXTRUDED ARTISAN SOAP HAVING INNER VEIN

FIELD OF THE INVENTION

The invention relates to extruded multiphase personal washing bars that have an artisan crafted appearance suitable for everyday use and to an extrusion process to make them. The bars include one or more inner veins of thermoplastic material within an extruded soap.

BACKGROUND

With the resurgence in the specialty soap market, consumers are being offered personal washing bars that have a much more hand crafted "one-of a kind" appearance—so called artisan soaps. Technically such bars have several characteristics that contribute to their distinctive appearance: i) sharpness of the boundary between the phases; ii) easily recognizable difference in optical texture and/or pattern that goes beyond color; and iii) a certain degree of bar to bar non-uniformity. Differences in optical texture and pattern are especially important to convey a collection of sensory expectations associated with bar.

To achieve a highly distinctive appearances, artisan soaps have been predominantly made by cast melt processes—either single casting or sequential multiple casts. For example, U.S. Pat. No. US 2003/0171232—2003 to Freeman et al discloses a decorative soap that contains soap inclusions that are coated with a glitter agent (metallic pigment) in a powder coater. The coating makes the soap inclusions resemble a mineral.

Although melt-cast processes can yield bars with highly controlled patterns, they are generally slow and labor intensive. Consequently, multiphase artisan soaps are relatively expensive and tend to be confined to upscale specialty shops and outlets. Furthermore, melt cast soaps are known to have high wear rates and mushing characteristics that make them less preferred for everyday use.

The objective of the present invention is a multiphase bar that has an unusual artisan-crafted appearance yet can be produced by an efficient high speed extrusion process and conventional stamping.

A further objective is an artisan bar that have wear rate and mushing properties characteristic of milled soap and is thus economical for everyday use.

U.S. Pat. No. 6,730,642 to Aronson et al describes an extruded soap in which is dispersed a second phase that is added as solid pieces prior to the final compaction step in billet formation. By controlling the hardness ratio of the two solids, deformation of dispersed phase during extrusion can be minimized thus producing bars with visually distinctive chunks or bits dispersed throughout.

The present work targets an extruded multiphase bar having a very different structure in which the inclusion is in the form of a veins or ribbon located in the interior of the bar. This structure produces an appearance that is reminiscent of a translucent natural mineral such as for example, quartz or opal in which inclusions of a different composition are visible or become visible veins within the mineral. Technically, this appearance arises from the inclusion having a substantial surface area being approximately spatially confined within to a relatively thin volume slice in the material, i.e. ribbon-like structure. The inclusions are also optically non uniform. When the mineral is translucent or transparent the vein or ribbon can be perceived deep within the material while if the mineral is opaque the vein is only visible when present very close to the surface or when the mineral is fractured or ground to expose the vein.

Various attempts to approximate a veined appearance in bars have been described in the soap art under the heading of variegated, marbled, striated, and striped soaps. Prior art has mainly focused on routes to reproducibly achieve spatial variation in dye or pigment concentration as the primary means of generating bars that appear as comprising multiple phases.

One commonly used technique to make striated soaps is to combination of different color noodles to form a mixture in for example the vacuum chamber of an extruder. This mixture is then extruded to form a billet which is then stamped into a bar. This method is disclosed in the following parents:

U.S. Pat. No. 3,673,294 to Matthaei et al, teaches a process to form multicolored bars by extruding a mixture of two noodles which are required to have the same viscosity and essentially the same hardness (penetration value).

U.S. Pat. No. 3,940,220 to D'Arcangeli teaches the extrusion of a mixture of two noodles in which it is required that the discontinuous phase be softer [lower penetration value] than the main soap.

U.S. Pat. No. 3,993,722, to Borcher et al and U.S. Pat. No. 4,092,388 to Lewis teaches processes of combining different colored noodles to formed marbled soap. The two noodles have essentially the same composition apart from colorant and the two different color noodles have essentially the same temperature at the time of extrusion.

U.S. Pat. No. 4,310,479 to Ooms et al teaches a process for combining a minor amount of opaque noodles with transparent noodles to form a transparent marbled bar. The noodles should differ in water content by no more than 3% and are at the same temperature during extrusion.

U.S. Pat. No. 6,390,797 to Meyers teaches a process for making marbleized or speckled soap by addition of a second stream of colored soap pellets into the inner of the final stage plodder at a specific point.

A second common method of producing striated soaps is the injection of a dye solution during extrusion. Examples of patents disclosing this type of process include:

U.S. Pat. No. 4,474,545 to Mazzoni teaches radial dye injection at nose cone entry and employs a rotor within nose cone to produce wavy stripes.

U.S. Pat. No. 3,676,538 Patterson teaches the injection of a saponaceous dye solution through screw of plodder at the pressure plate before nosecone to make marbled soaps.

U.S. Pat. No. 3,663,671 to Meye et al teaches injection of dye solution into at least two inlets in the jacket of the plodder of an extruder in set locations.

U.S. Pat. No. 3,832,431 to Matthaei discloses injection of dye in given rates, at specific point through the wall in the barrel of the final stage extruder to make marbled bars.

U.S. Pat. No. 4,304,745 to Alderson et al discloses soap extruded via single screw through a perforated plate having large holes at the periphery and small holes in the center. Dye is injected in the middle of the plate to form bars with large colored striped at surface.

U.S. Pat. No. 4,720,365 to Shonig et al discloses the addition of liquid dye after pressured exit of final extruder via a pressure plate which has multiple holes to form finely striated bars.

In both of the broad methods described above (extrusion of a combination of colored noodles and dye injection) the multicolored soap mass undergoes considerable extensional and/or shear flow during billet formation. Consequently, the numerous multiple striations so produced are randomly located throughout the bar and are generally elongate structures that individually have relatively small width in comparison with the overall width of the bar.

Coextrusion has also been used to make striped soaps. For example:

U.S. Pat. No. 3,884,605 to Grelon teaches an apparatus for making striated soap by coextrusion where it is desirable that the two soaps have identical material properties, e.g., hardness, apart from color.

U.S. Pat. No. 6,383,999 to Coyle et al teaches a coextruded multiphase bar in which the phases differ in the level of emollient but must have similar flow properties under extrusion process conditions.

WO 01/91990 to Trinque discloses a "soap striater" comprising a primary and perpendicular plodder feeding a tube partitioned chamber exiting a perforated pressure plate into a nose cone. Some of the apertures may be blocked to get different patterns U.S. Pat. No. 3,294,692 to Kelly et al discloses a striped bar made by injecting different colored masses into "grooved billet" through multiple extruders feeding a single chamber.

The coextruded bars described above have a pattern of distinctive multiple stripes which are uniformly distributed throughout the bar. Each stripe is visually uniform and occupies a relatively small cross sectional area relative to the overall area of the bar.

In contrast, the bars of the present invention have one or more inner veins. By inner vein we mean a ribbon-like, preferably non-uniform, structure that does not touch the surface of the bar when the bar is first produced, i.e., there is a layer of extruded soap between the vein and the surface of the bar. Furthermore, each vein is located approximately within a volumetric slice orientated in a horizontal plane between the top and bottom surfaces of the bar. By the term horizontal plane is meant a plane that is parallel to either a plane that is tangential to the bottom surface of the bar or to a plane that is tangential to the top surface of the bar. For most bars of commercial interest, these top and bottom tangential planes are essentially parallel.

Another distinguishing feature of the bars of the current invention is the expanse of the inner vein. In contrast to previous multi-phase extruded bars, the inner vein forms a contiguous mass (connected) that occupies a substantial portion of the area of the overall bar within the volumetric slice where it is predominantly located.

For example, if the outer extruded phase was transparent and the inner vein was opaque, then an individual vein when viewed through the bar in a direction perpendicular to the top face would be observed to occupy an area that is at least about 15% of the total cross sectional area of the bar (considered a substantial portion of the area), preferably at least 20%, more preferably at least 30% and most preferably greater than 50% of the total cross sectional area of the bar.

An alternative description of substantial expanse of the vein can be given in terms of a characteristic dimensions relative to the bar. One such characteristic dimension is the maximum width of the vein within a specified plane of the bar relative to the maximum width of the overall bar. Using again the above example of a transparent outer phase and an opaque vein, then the inner vein when viewed through the bar in a direction perpendicular to the top face would be observed to have a maximum width that is at least about 15% of the maximum width of the bar (considered a substantial fraction of the overall width of the bar), preferably at least 20%, preferably at least 25%, more preferably at least about 30% and most preferably greater than 50% of the maximum width of the bar. The term width is used here in its normal sense to designate the smaller orthogonal dimension of the bar in a plane perpendicular to the top face of the bar.

By the term "maximum width of the inner vein" is meant the width of the vein at its widest point. By the term "maximum width of the bar" is meant the width of the bar at its widest point.

Bars having these and additional characteristics and properties can be made by following the teachings of the present invention.

SUMMARY OF INVENTION

The personal washing bars of the invention are extruded and stamped bars that posses an artisan crafted appearance. Specifically, the extruded and stamped personal washing bar have top and bottom stamped faces bounded by a parting line or edge band and a horizontal plane intersecting the parting line or edge band. The bars further comprise an outer surfactant phase and an inner vein comprising a thermoplastic mass. The inner vein is located between the top and bottom stamped faces of the bar and a projection of the said inner vein onto the horizontal plane intersecting the parting line or edge band has a maximum width that is at least 20% of a maximum width of the bar in said horizontal plane.

In one embodiment of the invention the inner vein has an approximately elliptical cross section defined by a major axis and a minor axis wherein the ratio of the major axis to the minor axis is greater that about 3.

In another embodiment of the invention the volumetric slice containing the inner vein is approximately centered in a midpoint plane between the stamped faces of the bar.

The invention also encompasses a process for the manufacture of a multiphase soap bar including an inner vein. Specifically the process includes the steps of:

i) injecting a thermoplastic mass into an extruded soap mass undergoing substantially plug flow, said injection being directed parallel with the flow of the extruded soap so as to form a composite mass comprising an exterior extruded soap and an inner thermoplastic mass in the form of a cylinder,
ii) cutting the composite mass into billets,
iii) stamping the billet with a set of dies which when joined define a mold, wherein the stamping is in a direction perpendicular to the flow of the extruded soap so as to form a stamped bar having a top and bottom stamped surface bounded by a parting line or edge band and a horizontal plane intersecting the parting line or edge band;

wherein the thickness of the billet is sufficiently larger than the thickness of the mold such that the cylinder comprised of the thermoplastic mass spreads out in a direction orthogonal to the direction of stamping so as to form an inner vein wherein said inner vein is located between the top and bottom stamped faces of the bar and wherein a projection of the inner vein onto the horizontal plane intersecting the parting line or edge band has a maximum width that is at least 20% of a maximum width of the bar in said horizontal plane.

In another embodiment of the process of the invention, the stamping step iii) provides a sufficient spreading out of the cylinder having an equivalent cross sectional diameter 2R such that the inner vein so formed has a maximum width Wv, said stamping producing an expansion defined as Wv/2R that is greater than 2, preferably greater than 3, more preferably greater than 4 and most preferably greater than 5.

It should be understood that the invention also encompasses bars and process to prepare bars having multiple inner veins (two or more) provided that each inner vein and process steps meet the criteria set forth above.

These and other embodiments are described more fully below by written description to be read in conjunction with the accompanying drawings.

DETAILED DESCRIPTION OF INVENTION

Figure 1:
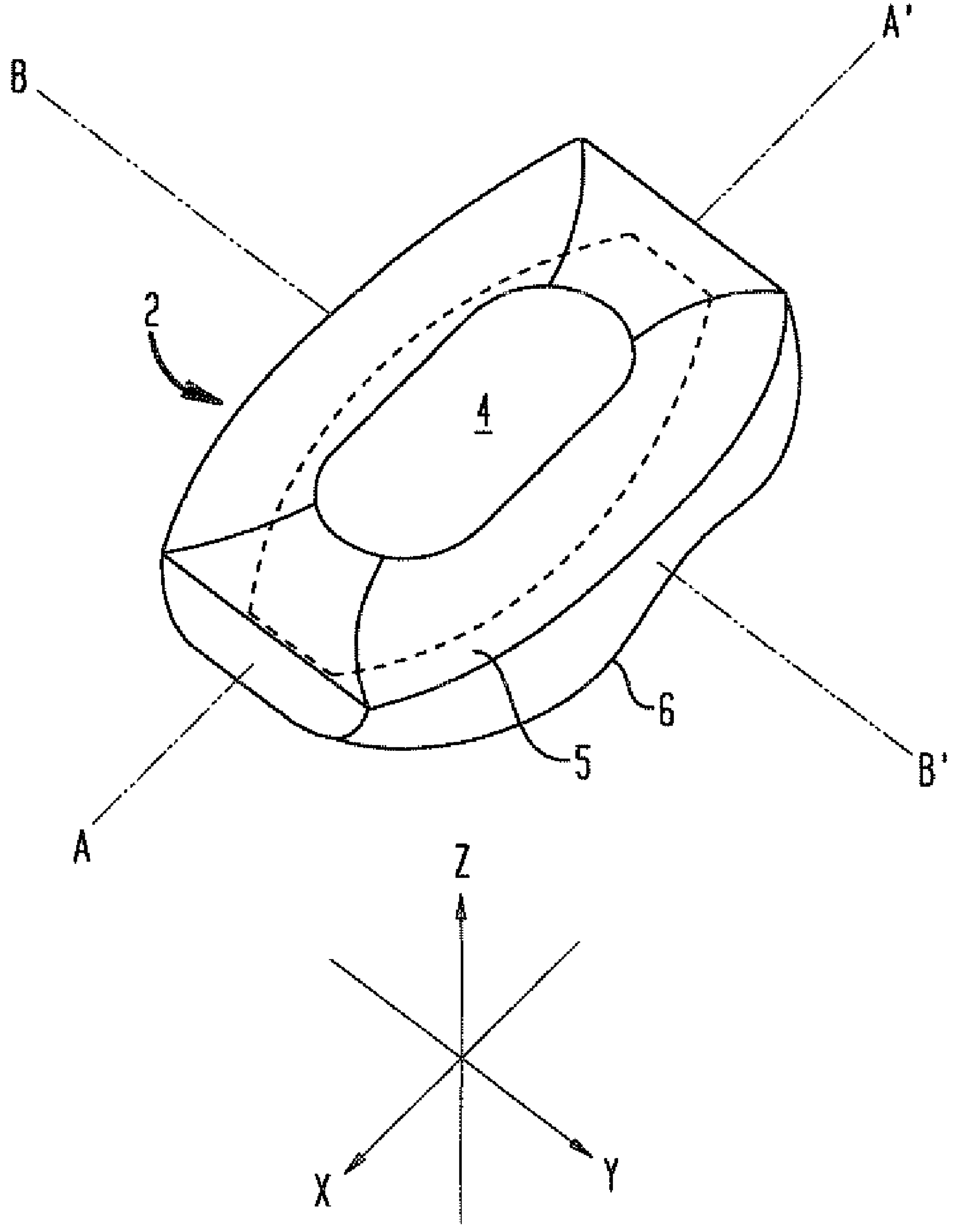
FIG. 1 Perspective view of bar.

As used herein % or wt % refers to percent by weight of an ingredient as compared to the total weight of the composition or component that is being discussed.

Except in the operating and comparative examples, or where otherwise explicitly indicated, all numbers in this description indicating amounts of material or conditions of reaction, physical properties of materials and/or use are to be understood as modified by the word "about." All amounts are by weight of the final composition, unless otherwise specified.

It should be noted that in specifying any range of concentration, any particular upper concentration can be associated with any particular lower concentration.

For the avoidance of doubt the word "comprising" is intended to mean "including" but not necessarily "consisting of" or "composed of." In other words, the listed steps, options, or alternatives need not be exhaustive.

The present invention relates to a multiphase soap bar having at least two key types of phases which have different compositions. One or more outer phases comprising an extruded surfactant phase and one or more inner phases comprising a thermoplastic mass. By the term "different composition" is meant that the outer and inner phases have at least one component that has a significantly different concentration in the two phases. Preferably the two phases also have different physical properties especially rheological properties, sensory properties which include, appearance (e.g., optical opacity and color), tactile properties (e.g., perceived creaminess), and/or olfactory properties (fragrance note or intensity).

Additionally, the inner phase is present as one or more inner veins having a defined geometrical relationship with respect to the outer extruded soap phase.

The nature of the outer and inner phases, their geometrical relationships in the bar and the preferred methods for producing the bar are described below. This description should be read in conjunction with the accompanying figures.

Outer Extruded Surfactant Phase

The outer extruded surfactant phase, hereafter also designated simply as the "outer phase" comprises one or more surfactants. The surfactant comprises from about 25% to about 95% by weight of the outer phase, preferably from about 50% to about 90% by weight and most preferably from about 60% to about 80% of the outer phase.

The surfactants should be suitable for routine contact with human skin and preferably be high lathering. A variety of surfactants can be employed such as those described in U.S. Pat. No. 6,730,642 to Aronson et al incorporated by reference herein.

One especially useful class of surfactants comprises fatty acid soaps. The term "soap" is used herein in its popular sense, i.e., the alkali metal or alkanol ammonium salts of aliphatic, alkane-, or alkene monocarboxylic acids. Sodium, potassium, magnesium, mono-, di- and tri-ethanol ammonium cations, or combinations thereof are suitable for purposes of this invention. In general, sodium soaps are used in the compositions of this invention, but from about 1% to about 25% of the soap may be potassium or magnesium soaps. The soaps useful herein are the well known alkali metal salts of natural of synthetic aliphatic (alkanoic or alkenoic) acids having about 8 to 22 carbon atoms, preferably about 10 to about 18 carbon atoms. They may be described as alkali metal carboxylates of branched of unbranched hydrocarbons having about 8 to about 22 carbon atoms.

Soaps having the fatty acid distribution of coconut oil may provide the lower end of the broad molecular weight range. Those soaps having the fatty acid distribution of peanut or rapeseed oil, or their hydrogenated derivatives, may provide the upper end of the broad molecular weight range.

It is preferred to use soaps having the fatty acid distribution of coconut oil or tallow, or mixtures thereof, since these are among the more readily available fats. The proportion of fatty acids having at least 12 carbon atoms in coconut oil soap is about 85%. This proportion will be greater when mixtures of coconut oil and fats such as tallow, palm oil, or non-tropical nut oils or fats are used, wherein the principle chain lengths are C16 and higher. Preferred soap for use in the compositions of this invention has at least about 85% fatty acids having about 12 to 18 carbon atoms.

Coconut oil employed for the soap may be substituted in whole or in part by other "high-lauric" oils, that is, oils or fats wherein at least 50% of the total fatty acids are composed of lauric or myristic acids and mixtures thereof. These oils are generally exemplified by the tropical nut oils of the coconut oil class. For instance, they include: palm kernel oil, babassu oil, ouricuri oil, tucum oil, cohune nut oil, murumuru oil, jaboty kernel oil, khakan kernel oil, dika nut oil, and ucuhuba butter.

A preferred soap is a mixture of about 15% to about 40% derived from coconut oil or other lauric rich oils and about 85% to about 60% tallow or other stearic rich oils.

The soaps may contain unsaturation in accordance with commercially acceptable standards. Excessive unsaturation is normally avoided.

Soaps may be made by the classic kettle boiling process or modern continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids, such as lauric (C12), myristic (C14), palmitic (C16), or stearic (C18) acids with an alkali metal hydroxide or carbonate.

A second type broad type of surfactant useful in the practice of this invention comprises non-soap synthetic type detergents—so called syndets. Syndets can include anionic surfactants, nonionic surfactants amphoteric or zwitterionic surfactants and cationic surfactants.

The anionic surfactant may be, for example, an aliphatic sulfonate, such as a primary alkane (e.g., $C_8$-$C_{22}$) sulfonate, primary alkane (e.g., $C_8$-$C_{22}$) disulfonate, $C_8$-$C_{22}$ alkene sulfonate, $C_8$-$C_{22}$ hydroxyalkane sulfonate or alkyl glyceryl ether sulfonate (AGS); or an aromatic sulfonate such as alkyl benzene sulfonate.

The anionic may also be an alkyl sulfate (e.g., $C_{12}$-$C_{18}$ alkyl sulfate) or alkyl ether sulfate (including alkyl glyceryl ether sulfates).

The anionic surfactant may also be alkyl sulfosuccinates (including mono- and dialkyl, e.g., $C_6$-$C_{22}$ sulfosuccinates) and alkyl ethoxy sulfosuccinates; alkyl and acyl taurates, alkyl and acyl sarcosinates, sulfoacetates, $C_8$-$C_{22}$ alkyl phosphates and phosphates, alkyl phosphate esters and alkoxyl alkyl phosphate esters, acyl lactates, $C_8$-$C_{22}$ monoalkyl succinates and mateates, sulphoacetates, and acyl isethionates.

Another class of anionics is $C_8$ to $C_{20}$ alkyl ethoxy (1-20 EO) carboxylates.

A preferred anionic surfactant is $C_8$-$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms. The acyl isethionate may also be alkoxylated isethionates Acyl isethionates, when present, will generally range from about 0.5 to about 50% by weight of the total composition. Preferably, this component is present from about 1 to about 15% and most preferably from about 1% to about 10% by weight.

In general the anionic component will comprise from about 1 to 20% by weight of the syndet surfactant base, preferably 2 to 15%, most preferably 5 to 12% by weight of the composition.

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. Suitable amphoteric surfactants include amphoacetates, alkyl and alkyl amido betaines, and alkyl and alkyl amido sulphobetaines.

Amphoacetates and diamphoacetates are also intended to be covered in possible zwitterionic and/or amphoteric compounds which may be used.

The amphoteric/zwitterionic surfactant, when used, generally comprises 0% to 25%, preferably 0.1 to 20% by weight, more preferably 1% to 10% of the surfactant base.

Suitable nonionic surfactants include the reaction products of compounds having a hydrophobic group and a reactive hydrogen atom, for example aliphatic alcohols or fatty acids, with alkylene oxides, especially ethylene oxide either alone or with propylene oxide. Examples include the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a alkyl polysaccharides and alkyl polysaccharide amides.

Examples of cationic detergents are the quaternary ammonium compounds such as alkyldimethylammonium halogenides.

Other surfactants which may be used are described in U.S. Pat. No. 3,723,325 to Parran Jr. and "Surface Active Agents and Detergents" (Vol. I & II) by Schwartz, Perry & Berch, both of which is also incorporated into the subject application by reference.

Although the surfactants comprising the outer phase may be entirely soap or syndet it is in some cases preferable to uses a combination of soaps with synthetic surfactants. Examples of combination bases are disclosed in U.S. Pat. No. 4,695,395 to Caswell, et al incorporated by reference herein.

In addition to surfactants, the outer phase can contain various optional ingredients including plasticizing agents, fillers, and various adjuvants. These are described below under OPTIONAL INGREDIENTS.

Regardless of which surfactants are used, the outer phase is an extruded phase, i.e., is made by extrusion. Thus, the outer phase must posses certain physico-chemical properties that allow the mass to be extruded efficiently by a high speed extrusion as practiced in modern soap finishing plants.

Several key properties are required for extrusion. First, the mass comprising the outer phase must be thermoplastic within the process temperature of extrusion which is generally between about 30° C. and about 50° C., preferably about 30° C. and about 45° C., and most preferably between about 33° C. and about 42° C. Thus, the material must soften within this process temperature window but remain highly viscous, i.e., not melt to a low viscosity liquid, and should harden quickly as the temperature is lowered.

Secondly, the softened mass although more pliable must be sufficiently viscous so that is does not stick to the surfaces of the extruder so as to be capable of conveyance by the extruder screws, and not bend excessively when exiting the extruder as a billet. However, if the mass is too viscous it will not be capable of extrusion at reasonable rates. It has been found that masses which exhibit a hardness value within a specified range as measured for example by penetrometer hardness tests (see TEST METHODOLOGIES section) are suitable for extrusion.

Thus, a key requirement for masses suitable for the outer phase of the invention is a hardness value as measured, for example, by the Cylinder Impaction Test (described below in the TEST METHODOLOGY section) that is within the range of about 20 lb/in$^2$ when measured at a temperature in the range of from about 30° C. to about 42° C. preferably a hardness of at least 28 when measured at a temperature in the range of about at 33° C. to about 42° C. In SI units 1 lb/in$^2$=6 894.76 pascal or about 8.9 kilopascals. It has been found from experience that when the hardness of the continuous phase falls within this range, it is possible to extrude the mass at a high rate. By high rate of production is meant in excess of about 50 tablet or bars per minute (4.5 Kg/min for a 90 Kg bar), preferably greater than about 150 bars per minute (13.5 Kg/min), and more preferably greater than 250 bars per minute (22.5 Kg/min).

Thus, so called melt and pour compositions such as those used to make glycerin soaps that require casting in molds in order to form bars are not suitable as the mass comprising the outer phase because they are not extrudable.

In one embodiment the outer phase is translucent or transparent provided it has the properties defined above that allows the mass to be extruded. The term "translucency" is typically determined in the art by noting the point size of Roman type letters that can be read clearly through a parallel-faced slice of soap 3 millimeters thick (see for example F. V. Wells, Transparent Soap, Soap and Chemical Specialties, June 1955). The method to quantify translucency used in the present work is the Soap Transparency Test set forth below in the TEST METHODOLOGY section.

It should be further noted that the outer extruded phase need not be a single homogeneous phase of a single composition. For example, the outer phase can contain discrete domains such as those described in U.S. Pat. No. 6,730,642 to Aronson et al, visible particles such as beads and microsperes. The outer phase can also include stripes or varigations.

The outer phase can also be composed of two or more coextruded streams of the different compositions. For example a bar comprised of two adjacent coextruded outer phase that are partially or completely separated by the vein phase is within the scope of the invention although this is not the preferred embodiment.

Inner Vein

The second phase comprising bars of the invention is the phase that makes up the inner vein. By the term "inner vein", alternatively designated simply as "vein" or "inner phase" is meant, with the aide of FIG. 1 and FIG. 2, a domain within the bar having at least some difference in chemical composition from the outer phase. This domain does not intersect the upper 4 or lower 6 faces of the bar, when the bar is made and has a ratio of its maximum width (width at widest point) projected in a horizontal XY plane Wv (FIG. 2B) to its maximum thickness (thickness at thickest point) in the orthogonal Z direction T2 (FIG. 2C) of greater than about 3, preferably greater than about 5 and most preferably greater than 10.

In the above definition, the lower surface is defined as the surface on which the bar is designed to rest in its most stable configuration on a supporting surface (e.g., sink or vanity) and the upper surface is the surface opposite the lower surface. Generally the lower surface is saddle shaped or has a dimple or well or other features designed to improve drainage and the upper surfaces frequently has an embossed logo.

The vein should preferably be substantially contained (at least 50% of the volume of the vein, preferably greater than 65%) within a volumetric slice oriented in a horizontal plane. The horizontal plane is defined as a plane parallel to the supporting plane of the bar where the supporting plane is that plane on which the bar is designed to rest against a horizontal supporting surface in its most stable configuration, e.g., in a soap dish.

Furthermore, in order for the vein to have significant visual impact or provide additional benefits to the bar (e.g., reinforcement) the geometric area occupied by the vein in the horizontal plane should be at least about 15% of the maximum geometric area of the bar bounded by its edges, e.g., parting line or edge band, preferably at least 25%, preferably at least 30%, more preferably at least about 50%, and most preferably greater than 75% of this maximum geometric area. By maximum geometric area of the bar bounded by its edges is meant essentially the geometric area of that horizontal plane bounded by edges with the greatest perimeter, i.e., the area of that horizontal slice with greatest area.

An alternative way to ensure high visual impact is in terms of the maximum width of the vein in a plane parallel to the top surface of the bar (or tangential to the top surface if the top surface is curved) relative to the overall width of the bar. The inner vein should have a maximum width that is at least about 20% (considered a substantial fraction of the overall width of the bar) of the maximum width of the bar, preferably at least 30% and more preferably greater than 50% of the maximum width of the bar. The term width is used here in its normal sense to designate the smaller orthogonal dimension of the bar in a plane perpendicular to the top face of the bar (The Y direction in FIG. 1).

One desirable embodiment of the invention is a bar wherein the vein is located in a volumetric slice that is approximately centered in a horizontal midpoint plane within the bar, e.g., a horizontal plane that is approximately centered on a horizontal plane passing through the parting line or a plane equally spaced between the top and bottom surfaces of the bar. Such positioning provides the greatest longevity in use of the visual impact or functional benefit provided by the vein.

The mass comprising the vein is also a thermoplastic composition in the sense defined above in connection with the outer phase. For the reasons discussed below in connection with the preferred process used to make the bars of the invention, it is desirable that the mass comprising the vein should not be harder (less pliable) than the outer phase at the average temperature at which the bar is stamped. Although chilled dies (molds) are often employed for high speed processes (−10° C. to about −6° C.), the average temperature of the interior of the masses is actually closer to the extrusion temperature (i.e., in the range of 30° C.-50° C.).

In one embodiment, the thermoplastic mass comprising the vein should preferably have a penetrometer hardness that is no greater than the penetrometer hardness of the outer phase when measured by the Cylinder Impaction Test at a temperature corresponding to the average temperature at which the composite billet is stamped. Preferably the penetrometer hardness of the mass comprising the vein should have at least about a 10% lower hardness than the outer phase, more preferably at least about a 15% lower hardness and most preferably at least about a 20% lower hardness that the outer phase when measured by the Cylinder Impaction Test at a temperature corresponding to the average temperature at which the composite billet is stamped, generally between about 30° C. and about 45° C., e.g., 35° C. and about 40° C.

The mass comprising the vein preferably contains one or more surfactants of the types similar to or the same as those used in the outer phase and discussed above. Preferred surfactants include tatty acid soaps, fatty isethionate, and a combination of these two types of surfactants. However, both the types and amounts of surfactants in the outer phase and the vein can be the same or different. It is preferable that the mass of the inner vein comprises one or more surfactants at a level of at least about 25% by weight of the mass comprising the inner vein, more preferably at least about 40% and most preferably at least about 50% by weight of the inner vein The vein mass can also include non surfactant materials provided they yield thermoplastic solids. These can be water soluble or water insoluble materials. Examples include polyalkylene glycols such as polyethylene oxide, polypropylene oxides or their copolymers; branched or unbranched wax alcohols or alkoxylates such as self dispersible waxes; polyesters, and other thermoplastic polymers.

Polyalkylene glycol having a melting point above 30° C. is particularly useful. Preferably, the polyalkylene glycol should have a molecular weight greater than about 4,000 to about 100,000, preferably about 4000 to about 20,000, most preferably about 4000 to about 10,000. Minimum MW of about 4000 is believed required so that inner mass is solid at room temperature. A suitable polyalkylene glycol is polyethylene glycol, for example Carbowax® PEG 8000.

Hydrophobically modified polyalkylene glycol (HMPAG) having broad molecular weight 4,000 to 25,000, preferably 4,000 to 15,000 can also be employed. Generally, the polymers will be selected from polyalkylene glycols chemically and terminally attached by hydrophobic moieties, wherein the hydrophobic moiety can be derivatives of linear or branched alkyl, aryl, alkylaryl, alkylene, acyl (e.g., preferably $C_8$ to $C_{40}$; fat and oil derivatives of alkylglyceryl, glyceryl, sorbitol, lanolin oil, coconut oil, jojoba oil, castor oil, almond oil, peanut oil, wheat germ oil, rice bran oil, linseed oil, apricot pits oil, walnuts, palm nuts, pistachio nuts, sesame seeds, rapeseed, cade oil, corn oil, peach pit oil, poppyseed oil, pine oil, soybean oil, avocado oil, sunflower seed oil, hazelnut oil, olive oil, grapeseed oil, and safflower oil, Shea butter, babassu oil, etc. The total content of the hydrophobic moiety is preferably 3% wt. to 15% wt. per mole of the defined HMPAG.

Fatty acids, fatty acid esters, and fatty alcohols can be incorporated as part of the inner phase mass. Generally, the fatty group has a chainlength between 12 and 22 carbon atoms. Particularly suitable fatty acid ester is glycerol monolaurate.

Still other useful non-surfactant materials are derived from polysaccharides especially starch. These include unmodified starch; starch modified to alter its water solubility, dispersability, and swelling, and hydrolyzed starch such as maltodextran.

Optional Ingredients

Plasticizing Agents

A useful component especially for the mass comprising the inner vein is a plasticizing agent. Here we define plasticizing agent as a material that may alter both the hardness and the consistency of the continuous phase, especially at temperatures at which the multiphase bar is stamped. Without being bound by theory, these materials are thought to facilitate both the outward flow of the inner vein mass during stamping and to facilitate a stronger bond between vein and the outer phase that resists cracking or fracture during use.

A variety of materials can be used as a plasticizer: the key property is that they alter the hardness of the mass or masses at the required temperature.

Oils are particularly useful plasticizers. One useful class of oils is ester oils: oils having at least one ester group in the molecule, especially fatty acid mono and polyesters such as cetyl octanoate, octyl isonanoanate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate; sucrose ester, sorbitol ester, and mixtures thereof.

Triglycerides and modified triglycerides (e.g., ethoxylated triglycerides) are particularly useful ester oils. These include vegetable oils such as jojoba, soybean, canola, sunflower, palm, safflower, rice bran, avocado, almond, olive, sesame, persic, castor, coconut, and mink oils. These oils can also be hardened to remove unsaturation and alter their melting points. Synthetic triglycerides can also be. Some modified triglycerides include materials such as ethoxylated and maleated triglyceride derivatives. Proprietary ester blends such as those sold by Finetex as Finsolv® are also suitable, as is ethylhexanoic acid glycerides.

Another type of useful ester oil is liquid polyester formed from the reaction of a dicarboxylic acid and a diol. An example of polyesters suitable for the present invention is the polyesters marketed by ExxonMobil under the trade name PURESYN ESTER®.

A second class of oils suitable plasticizing agent for the present invention is hydrocarbon oil. This includes linear and branched oils such as liquid paraffin, squalene, squalane, mineral oil, low viscosity synthetic hydrocarbons such as polyalphaolefin sold by ExxonMobil under the trade name of PureSyn PAO® and polybutene sold under the trade name PANALANE® or INDOPOL®. Highly branched hydrocarbon oils may also be suitable. Although more properly classified as a grease, petrolatum can also serve as a useful plasticizer.

Some natural and synthetic waxes can also be used as plasticers providing they have the correct melting point and solubility properties.

A third type of material that can function as a plasticizer are C8-C22 fatty acids, preferably C12-C18, preferably saturated, straight-chain fatty acids. However, some unsaturated fatty acids can also be employed. Of course the free fatty acids can be mixtures of shorter (e.g., C10-C14) and longer (e.g., C16-C18) chain fatty acids although it is preferred that longer chain fatty acids predominate over the shorter chain fatty acids.

The fatty acid can be incorporated directly or be generated in-situ by the addition of protic acid. Examples of suitable protic acids include: HCL, adipic acid, citric acid, glycolic acid, acetic acid, formic acid, fumaric acid, lactic acid, malic acid, maleic acid, succinic acid, tartaric acid and polyacrylic acid. Other protic acids are mineral acids such as hydrochloric acids, phosphoric acid, sulfuric acid and the like.

Nonionic surfactants can also serve as plasticizers for the continuous phase. Nonionic surfactant in the context of instant invention are amphiphilic materials in which the polar groups are uncharged. Examples of suitable nonionic surfactants include: ethoxylates (6-25 moles ethylene oxide) of long chain (12-22 carbon atoms) fatty alcohol (ether ethoxylates) and fatty acids; alkyl polyhydroxy amides such as alkyl glucamides; alkyl polyglycosides; esters of fatty acids with polyhydroxy compounds such as glycerol and sorbitol; ethoxylated mono-, di- and triglycerides, especially those that have lower melting points; and fatty amides.

Organic bases, especially alkoxy amines like triethanolamine are also useful plasticizers when the surfactant employed is predominantly soap.

Hardening Agents

Hardening agents which can increase the hardness or reduce the pliability of the phases are useful optional ingredients.

Polyols and inorganic electrolytes are useful hardening agents especially when one or more of the phases are comprised predominantly of fatty acid soaps. Polyols are defined here as molecules having multiple hydroxyl groups. Preferred polyols include glycerol, propylene glycol, sorbitol, various other sugars and polysaccharides, and polyvinyl alcohol.

In addition to increasing hardness, polyols can also be used to increase the translucency of the outer phase to allow the inner vein to be visualized.

Preferred inorganic electrolytes include monovalent chloride salts, especially sodium chloride; monovalent and divalent sulfate salts like sodium sulfate, sodium carbonate; monovalent aluminate salts, monovalent phosphates, phosphonates, polyphosphate salts; and mixtures thereof. Further, the bar composition of the invention may include 0 to 25% by weight of crystalline or amorphous aluminium hydroxide. The said aluminium hydroxide can be generated in-situ by reacting fatty acids and/or non-fatty mono- or polycarboxylic acids with sodium aluminate, or can be prepared separately by reacting fatty acids and/or non-fatty mono- or polycarboxylic acids with sodium aluminate and adding the reaction product to the soap.

Another class of hardening agents are insoluble inorganic or mineral solids that can structure the phase by network formation or space-filling. These include fumed, precipitated or modified silica, alumina, calcium carbonate, kaolin, and talc. Alumino-silicate clays especially synthetic or natural hectorites can also be used.

Adjuvants

A wide variety of optional ingredients can be incorporated in one or more of the phases that comprise the bar composition. Examples of adjuvants include but are not limited to: perfumes; pearlizing and opacifying agents such as higher fatty acids and alcohols, ethoxylated fatty acids, solid esters, nacreous "interference pigments" such as $TiO_2$ coated micas; dyes and pigments; sensates such as menthol and ginger; preservatives such as dimethyloldimethylhydantoin (Glydant XL1000), parabens, sorbic acid and the like; anti-oxidants such as, for example, butylated hydroxytoluene (BHT); chelating agents such as salts of ethylene diamine tetra acetic acid (EDTA) and trisodium etridronate; emulsion stabilizers; auxiliary thickeners; buffering agents; and mixtures thereof.

Skin Benefit Agents

A particular glass of optional ingredients highlighted here is skin benefit agents included to promote skin and hair health and condition. Potential benefit agents include but are not limited to: lipids such as cholesterol, ceramides, and pseudoceramides; humectants and hydrophilic skin conditioning agents such as glycerol, sorbitol, propylene glycol, and polyalkalene oxides polymers and resins; antimicrobial agents such as TRICLOSAN; sunscreens such as cinnamates; exfoliant particles such as polyethylene beads, walnut shells, apricot seeds, flower petals and seeds, and inorganics such as silica, and pumice; additional emollients (skin softening agents) such as long chain alcohols and waxes like lanolin; additional moisturizers; skin-toning agents; skin nutrients such as vitamins like Vitamin C, D and E and essential oils like bergamot, *citrus unshiu, calamus*, and the like; water soluble or insoluble extracts of avocado, grape, grapeseed, myrrh, cucumber, watercress, *calendula*, elder flower, *geranium*, linden blossom, amaranth, seaweed, *gingko*, ginseng, carrot; *impatiens balsamina*, camu camu, alpina leaf and other plant extracts, and mixtures thereof.

The composition can also include a variety of other active ingredients that provide additional skin (including scalp) benefits. Examples include anti-acne agents such as salicylic and resorcinol; sulfur-containing D and L amino acids and their derivatives and salts, particularly their N-acetyl derivatives; anti-wrinkle, anti-skin atrophy and skin-repair actives such as vitamins (e.g., A, E and K), vitamin alkyl esters, minerals, magnesium, calcium, copper, zinc and other metallic components; retinoic acid and esters and derivatives such as retinal and retinol, vitamin B3 compounds, alpha hydroxy acids, beta hydroxy acids, e.g. salicylic acid and derivatives thereof; skin soothing agents such as aloe vera, jahoba oil, propionic and acetic acid derivatives, fenamic acid derivatives; artificial tanning agents such as dihydroxyacetone; tyrosine; tyrosine esters such as ethyl tyrosinate and glucose tyrosinate; skin lightening agents such as aloe extract and niacinamide, alpha-glyceryl-L-ascorbic acid, aminotyroxine, ammonium lactate, glycolic acid, hydroquinone, 4 hydroxyanisole, sebum stimulation agents such as bryonolic acid, dehydroepiandrosterone (DHEA) and orizano; sebum inhibitors such as aluminum hydroxy chloride, corticosteroids, dehydroacetic acid and its salts, dichlorophenyl imidazoldioxolan (available from Elubiol); anti-oxidant effects, protease inhibition; skin tightening agents such as terpolymers of vinylpyrrolidone, (meth) acrylic acid and a hydrophobic monomer comprised of long chain alkyl (meth)acrylates; anti-itch agents such as hydrocortisone, methdilizine and trimeprazine hair growth inhibition; 5-alpha reductase inhibitors; agents that enhance desquamation; anti-glycation agents; anti-dandruff agents such as zinc pyridinethione; hair growth promoters such as finasteride, minoxidil, vitamin D analogues and retinoic acid and mixtures thereof.

Test Methodology

Bar Hardness

A variety of methods are known in the art to measure the hardness of soft solids such as toilet soaps. The techniques have been used here is the Cylinder Impaction Test which measures the maximum force before yielding or fracture. However, other types of penetration test which measure the penetration of a needle or tapered rod under a constant load can be employed as well as micro-indentation techniques and those based on the use of a cheese wire. Although the invention is described by parameters that are measured by the Cylinder Impaction Test, various alternative hardness tests can be used and inter-correlated with the method used herein.

Cylinder Impaction Test for Hardness

The hardness of the continuous and dispersed phase was measured on extruded and compacted samples using the Cylinder Impaction Test employing a modified Crush-Test protocol that is used for measuring carton strength. A Regmed Crush Tester was employed.

Samples (typically 8×5×2 cm) at the desired temperature were placed on the lower plate of the tester fitted with a pressure gauge and a temperature probe inserted in the sample approximately 4 cm from the test area. An 89 gm inox metallic cylinder (2.2 cm in diameter (0.784 in) and 3 cm in length (1.18 in)) was placed at a central location on the top of the sample. The upper plate was then lowered to just touch cylinder.

The top plate was then lowered at a programmed rate of 0.635±0.13 mm/s (0.025±0.005 in/s). At a certain strain, the sample will yield, bend or fracture and the maximum force expressed as PSI (lbs/inch$^2$) and average sample temperature are recorded. The water content of the sample was measured immediately after the test by microwave analysis. The hardness measurement was repeated a total of 3 times with fresh samples and an average taken. It is important to control the temperature and water content of the sample since hardness is sensitive to both these variables.

Wear Rate—Controlled Rubbing Test

The intrinsic wear rate of the mass, e.g., individual phases or finished bar is measured by the following procedure.

a) Place 4 weighed tablets of each test batches on soap trays that have been coded as follows:

| With drainers | Wash temperature (° C.) |
|---|---|
| Yes | 25 |
| Yes | 40 |
| No | 25 |
| No | 40 |

b) Pour 10 ml distilled water (ambient temperature) into the undrained tray (25° and 40° C.).

c) Carry out washdowns on each tablet of soap as follows:

Fill washing bowl with about 5 litres of water, at the desired temperature (20° C. or 40° C.).

Mark the tablet to identify top face (e.g. make small hole with a needle).

Wearing waterproof gloves, immerse the tablet in the water, and twist 15 times (180° each time) in the hands above water.

Repeat the above step

Briefly immerse tablet in the water to remove lather.

Place tablet back on its soap tray, ensuring that the opposite face is uppermost (i.e. the unmarked face).

d) Carry out the full washdown procedure (step C) 6 times per day for 4 consecutive days, at evenly spaced intervals during each day (e.g. 9.00, 10.00, 11.00, 13.00, 14.00, 15.00). Alternate the face placed down after each washdown.

e) Between washdowns the soap trays should be left on an open bench or draining board, in ambient conditions. After each washdown cycle, change the position of each soap tray/tablet, to minimise variability in drying conditions.

f) At the end of each day:

rinse and dry each soap tray with drainer drain and refill the soap tray without drainer (24° C. and 40° C.) with 10 ml distilled water (ambient temperature). Consider water hardness of the country.

g) After the last washdown (i.e. Thursday afternoon) rinse and dry all soap trays, and place each tablet on its soap tray.

h) On the 5th day afternoon, turn the samples so that both sides of the tablet dry.

i) On the 8th day, weigh each tablet.

The rate of wear is defined as the weight loss in grams or percentage.

Wear=(initial weight−final weight)*100%=Result in percentage initial weight

Wear=(initial weight−final weight)=Result in grams initial weight

Soap Transparency Test

The degree of transparency was measured using a light transmission tester model EVT 150 manufactured by DMS—Instrumentacao Cientifica Ltd. The instrument consists of a light source providing a 1.5 cm circular beam, a detector fitted to an analog meter, and a sample holder. The measurement procedure is as follows.

The instrument is first set to 100% transmission in air (i.e., without a test sample). The test sample of the bar material, approximately 90 g, having a thickness of 3 cm is placed in the sample chamber and the % transmission relative to air is measured. Normal opaque soap bars have 0% transmission, while translucent bars have a transmission ranging from about 5 to about 40%. Highly transparent bars such as those made by melt-cast processes have a transmission generally greater than 45%.

It has been found that discontinuous phase compositions having a % transmission difference relative to the continuous phase of greater than about 5% are perceived as visually distinctive. Preferably, the difference in light transmission between the phases should be greater than 10%.

Bar Manufacturing Process

The bars of the invention were made by first forming a composite billet in which the inner thermoplastic mass, which ultimately becomes the vein, was injected into a defined location within the outer extruded surfactant phase. The injected inner mass can take a variety of geometrical forms. For example it can be a right cylinder of regular geometric cross section such as a circle or ellipse. Alternatively the injected mass can have a prismatic or bar shape with a rectangular, triangular or square cross section. Furthermore, the cross sectional area of the injected inner mass can be constant or it can vary along its length, i.e., undulating cylinder. Alternatively the cross section of the injected inner mass can be of a non-standard geometrical form such a tear drop, star, or petal shape.

Regardless of the specific shape of the cross section, it is preferable that the long access of the inner mass within the billet should be substantially parallel with the long access of the billet.

The outer surfactant phase, e.g., soap, was produced in a standard toilet soap finishing line using processing techniques and equipment well known in the art.

The first step of this process involves the mixing of dried soap noodles from storage silos with the minor ingredients in a batch mixer such a “z-blade” mixer. The objective of this operation is to generate a uniform distribution of the minor ingredients throughout the bulk of the soap batch until uniform coating of the noodles has occurred.

After mixing, the soap mass is generally passed through a refiner followed by a roll mill, e.g., 3-roll mill, to achieve micro-mixing and improve composition uniformity.

The same basic steps of blending, refining and milling are also used to separately prepare the inner thermoplastic mass. For continuous process, duplicate sets of mixers, refiners and mills may be employed with each set appropriately matched to the volumes and throughputs required for each of the two phases. Alternatively, the inner phase can be formed utilizing the same equipment as used for the continuous phase and then stored separately, (e.g., as noodles) until use.

Figure 3:
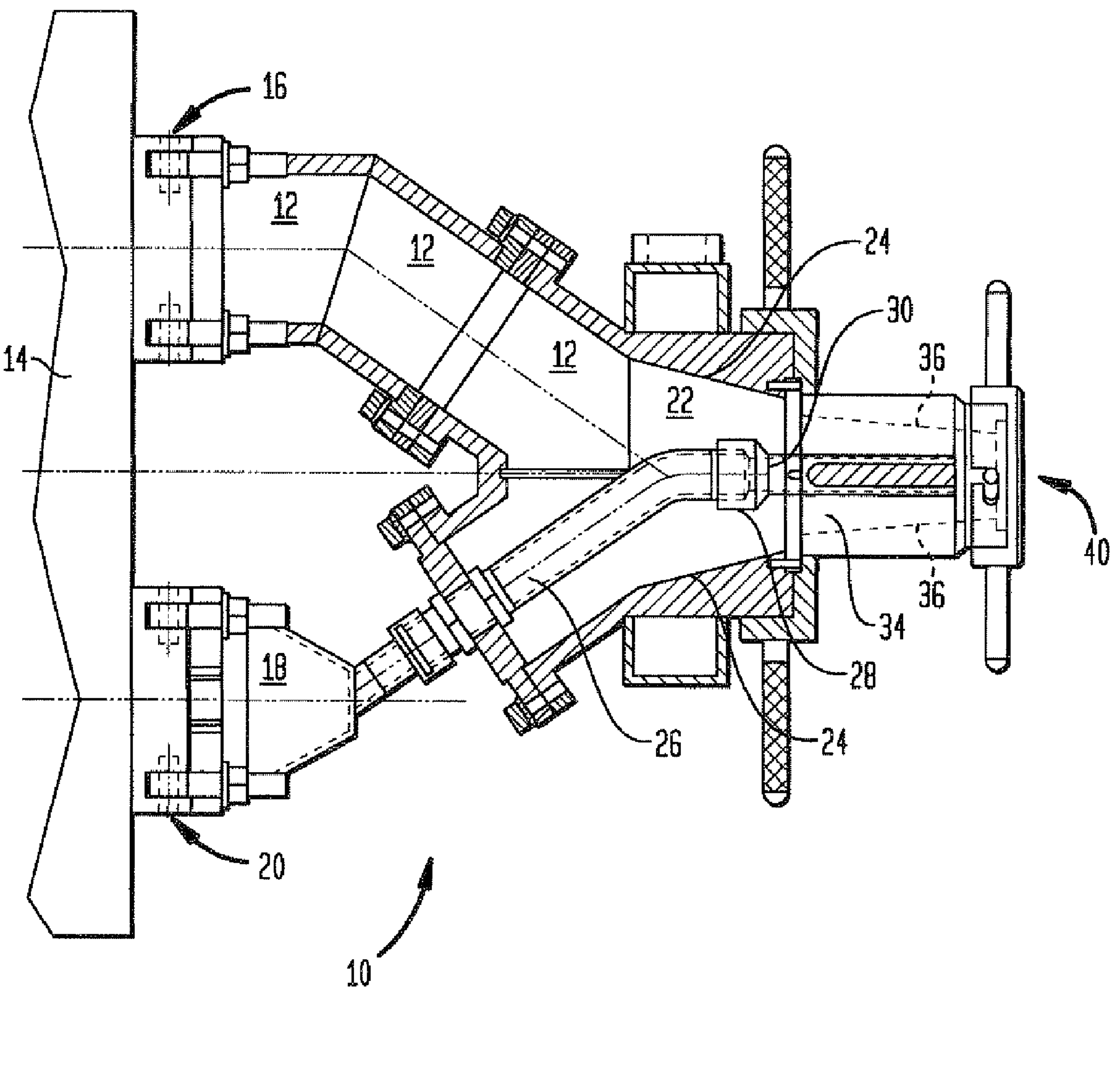
FIG. 3. Schematic diagram of vein injector (single vein).

In the billet forming process employed herein, the two phases are fed into a specially constructed tube coextrusion apparatus (designated an “injector assembly” 10) shown schematically in FIG. 3. This injector assembly can be fed with the inner and continuous phases either from a twin screw extruder with non-intermeshed screws or from separate extruders of appropriately matched throughputs. In either case final extrusion through the injector assembly is carried out at a temperature between about 30° C. and about 42° C. In one embodiment the injector assembly 10 includes an upper channel 12 joined to a face plate 14 that is affixed to a twin screw extruder (not shown) at the outer phase inlet port 16 and a lower channel 18 joined to the face plate affixed to the twin screw extruder (not shown) at the inner phase inlet port 20. The upper channel 12 is continuous with the pre-injection chamber 22 having tapered walls 24. The lower channel 18 is coupled to a tube 26 which in turn is coupled 28 to an inner phase exit port 30 having an aperture chosen to achieve the desired cross sectional shape of the inner phase mass. The outer phase and the inner phase are simultaneously fed through the upper and lower channels 12 and 18 and inner tube 26 into the injection chamber 34 where the composite billet is formed. The inner walls 36 of the injection chamber 34 are slightly tapered to compact the mass which aides in the cohesion of the outer and inner phases. The composite billet emerges from the exit port 40, having for example, a 3.5×3.5 cm cross section (adjustable), where it is cut by any convenient cutting means such as a knife or wire (not shown) into billets of the desired length, e.g., 7.4 cm.

It is desirable that injection and final transport of the composite billet through the injection chamber 34 occurs as close as possible to conditions of plug flow by which is meant that there is a minimum relative transverse or tangential shear taking place within the injection chamber 34. That is to say all volume elements along a cross sectional slice through the billet move as close as possible or practical in the same relative direction and at the same speed.

Although the injection process has been described using a specifically designed tube injector assembly (FIG. 3) other commercially available instruments such as those manufactured by the Mazzoni Company can be employed. One such example is the tube extruder described in U.S. Pat. No. 3,884,605 to Pierre Grelon. Such an extruder can adapted for the present purpose by blocking all but one or a few central medial tube(s) of the extruder so that the central vein precursor cylinder is injected at the proper location and significantly modified. However, such instruments are designed to produce striped bars in which the stripes experience minimal expansion during stamping. To use these instruments for the present application which requires extensive expansion during stamping, they must be adapted to provide the correct size tube (cross section) and size (volume) billet so that the composite billet is such that upon stamping the cylinder will actually spread out and expand sufficiently so as to actually form interior veined bars having the geometrical characteristics as disclosed herein.

Figure 4:
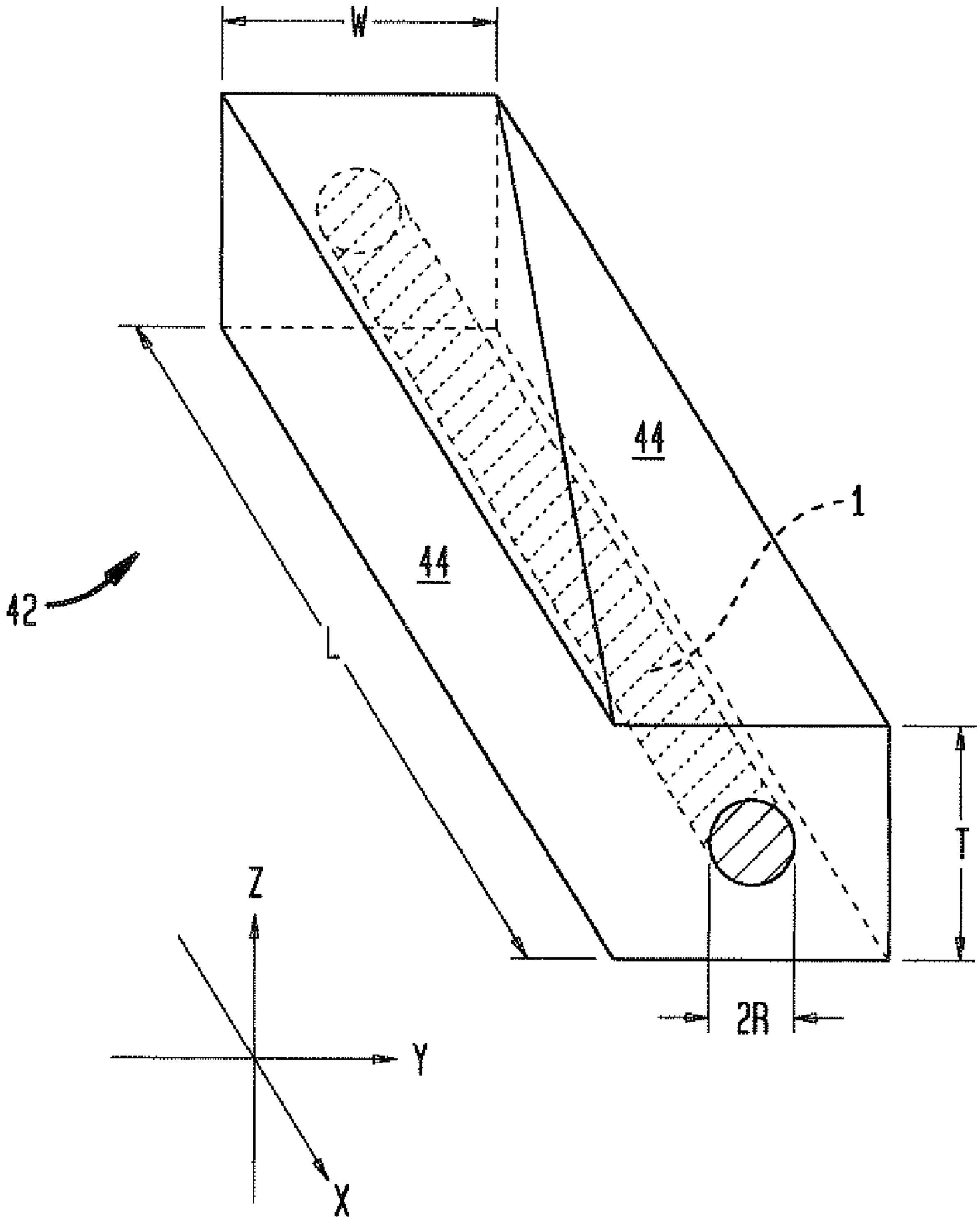
FIG. 4. Perspective view of composite billet showing an example of inner phase cylinder (in this case right circular cylinder) that becomes a vein after billet is stamped.

An example of a billet 42 so formed is shown schematically in FIG. 4. With reference to the XYZ plane convention shown in FIG. 4, the billet 42 with outer phase 44 has a thickness T, a width W and a length L. The inner phase 46 has a cylindrical form which in this example is a right circular cylinder geometry of cross sectional diameter 2R. However, it should be understood that the terms cylinder or cylindrical are used in their broadest sense to denote solid geometrical forms of arbitrary cross section having some form of translational repetition in the direction of flow.

The billet formed in the process described above is then stamped in a toilet soap stamping apparatus which generally comprising split dies. The dies when in the closed position form a mold of defined shape and volume. It is preferable to use capacity dies to form the finished bars of the invention. These dies compress a billet having a larger volume than the volume capacity of the mold (the space or cavity defined by the dies when they are brought into contact) thus ensuring that the soap is squeezed into all parts of the mold. The excess soap is exuded out of the mold from the edges of the mold. This excess soap commonly known as the flashing is then removed from the outer edge surfaces of the dies and generally recycled (see FIG. 5 item 54—note that for simplicity only the flashing squeezed out from the sides of the mold is shown)

Figure 5:
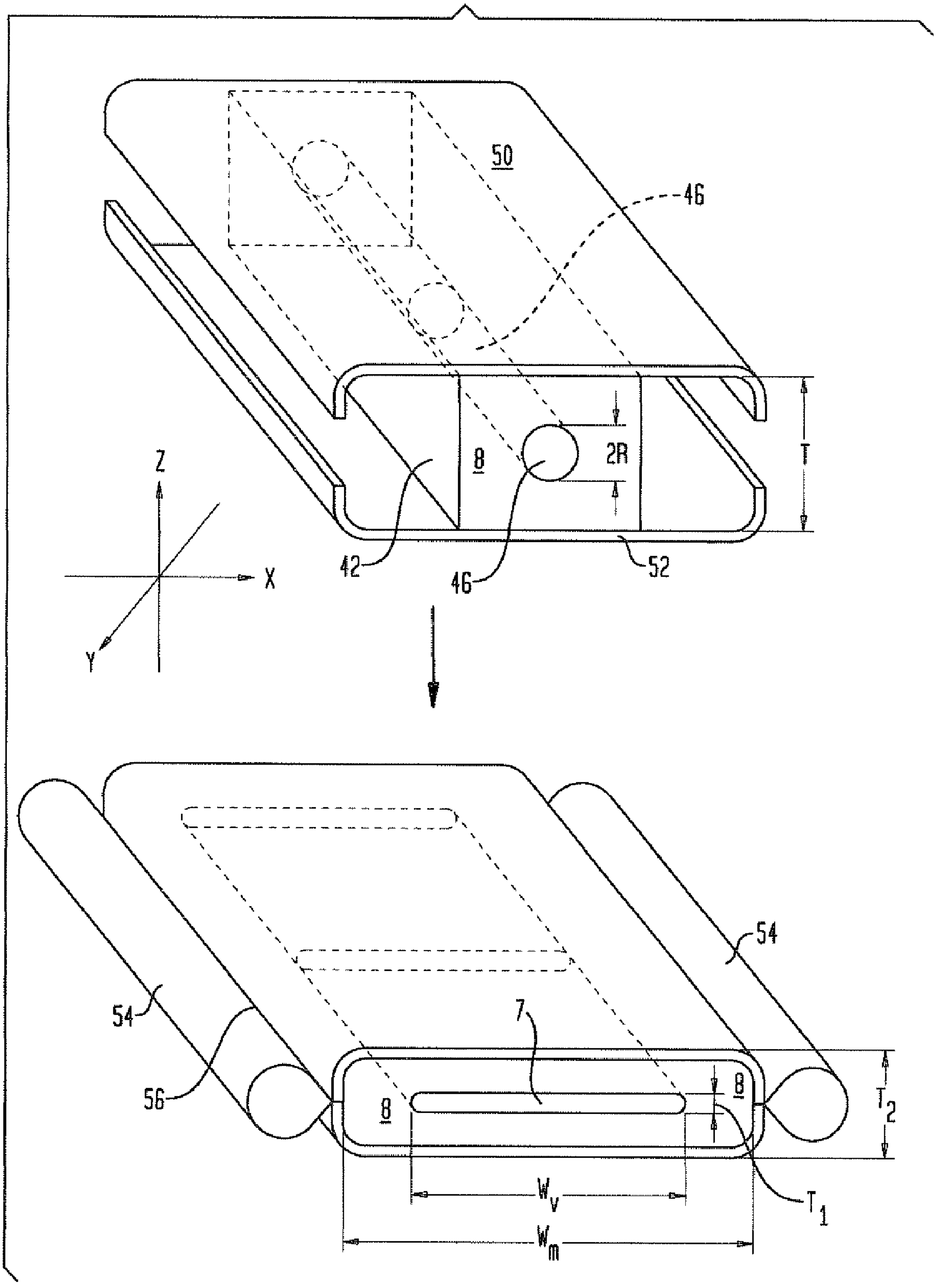
FIG. 5. Idealized illustration of stamping of composite billet: A—open mold dies just touch surface of billet; B—dies joined to define mold.

The process of stamping the composite billet is shown schematically in a simplified form in FIG. 5. When the billet 42 is compressed by dies 50 (top die—top half of mold) and 52 (bottom die—bottom half of mold) in a direction perpendicular to the long access of the inner phase 46, i.e., is the Z direction, the billet 42 is squeezed and deforms in the X,Y plane. Since the inner phase is pliable it will flatten to increase its cross sectional width and decrease its cross-sectional thickness. The final shape of the vein so formed from the expansion of the inner phase during stamping depends on the initial shape and dimensions of the cross-section of the inner phase 46 and the extent of expansion during stamping. The extent of expansion during stamping is in turn governed by the dimensions of the billet relative to the dimensions and shape of the mold formed by the closed dies.

If the molds were to have a simple block shape (parallel opposing walls) the extent of expansion of a cylindrical inner phase of radius R is approximately given by $$W_v/2R=\pi/4(T/T_2)$$

where $W_v$ is the final width of the vein, T is the thickness of the billet and $T_2$ is the thickness of the molded bar. The above equation is the limiting 2-dimensional approximation for a billet constrained only to expand in the X direction between infinite flat plates.

However, in practice commercial bars have streamlined shapes with distinctly curved surfaces and limited flat surfaces (landings). Moreover, some expansion of the billet also takes place in the Y direction. With real molds providing such shapes, more expansion of the inner phase takes place during the stamping than would be estimated from Eq. 1 because a greater volume of material is exuded in narrower regions of the mold bounded by the curved surfaces.

In a preferred embodiment, the cross sectional shape and dimensions of the inner phase and billet are chosen to achieve an expansion, defined as $W_v/2R$, of greater than about 2, preferably greater than 3 and more preferably greater than about 4, and most preferably greater than 5. Although the process is illustrated with a circular cylinder, the expansion can be generalized by defining an "equivalent circular diameter" for any arbitrary cross-sectional shape defined as the diameter of a circle having the same cross sectional area as the cross section of interest.

Figure 2A:
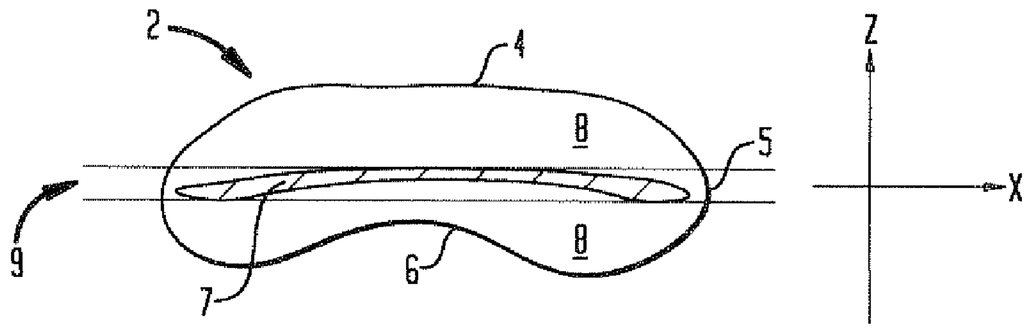
FIG. 2. Cross sectional schematic views of composite bar: A) X-Z plane side along A-A' cross section through XZ plane (FIG. 1); B) X-Y perpendicular to top surface 4 of FIG. 1; C) Y-Z plane along B-B' (FIG. 1).
Figure 2B:
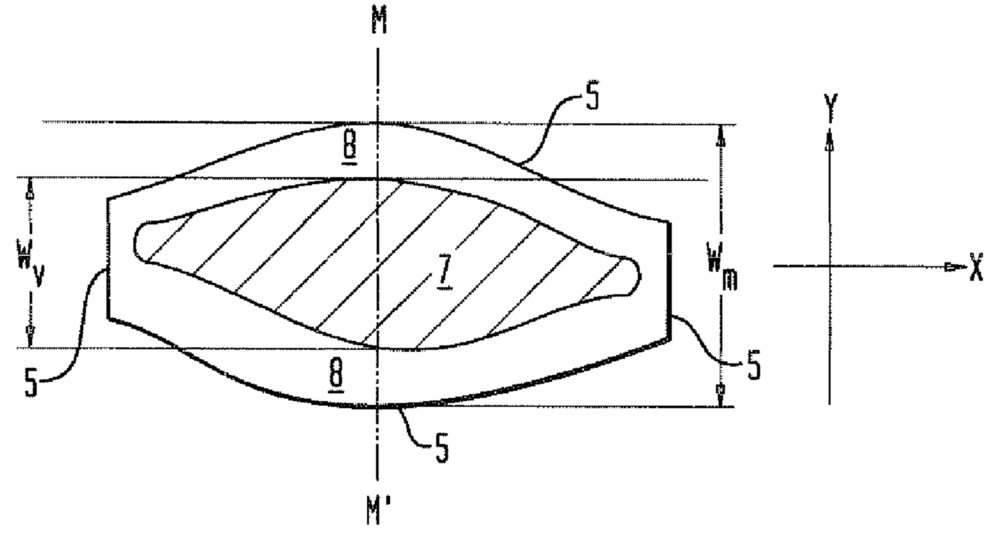
Figure 2C:
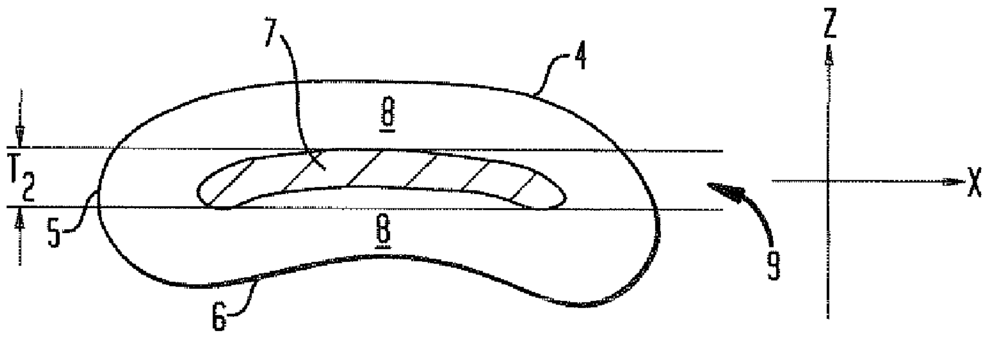

To achieve a significant visually impact, the maximum width $W_v$ (FIG. 2B and FIG. 5) of the vein should preferably be at least about 20%, preferably at least about 25%, more preferably at least 50% and most preferably at least 75% of the maximum width of the bar Wm (FIG. 2B and FIG. 5), said maximum bar width (width referring to smaller dimension in a plane perpendicular to the top surface of the bar, e.g., B'-B' in FIG. 1) and generally occurring in a horizontal plane passing through the parting line (line where to top and bottom dies come into contact (56 FIG. 5).

Although not essential, it is desirable that the inner phase does not expand so much that it exudes appreciably from the edges of the dies as flashing 54 as the dies come together, i.e., so that the flashing contains primarily or completely only the outer phase. In this way, the flashing 54 can be recycled to the outer phase stream without appreciably altering its composition and changing for example its optical properties, i.e., translucency or color. In particular, it is preferable that the flashing contains less than 2% by wt of the inner phase, more preferably less than 1% by weight of the inner phase. Most preferably the flashing should not contain any of the inner phase composition; a condition shown schematically in FIG. 5.

Another way to minimize the amount of inner phase in the flashing is to control the length of the inner phase within the billet by adjusting the flow of material in the inner phase feed stream FIG. 3 items 18, 26, 28 so that a space of pure outer surfactant composition is interspaced between cylinders (more generally columns) of inner phase. The distance between the columns is adjusted so that billets so formed will not exude inner phase at the ends of mold during stamping.

The final shape of the vein formed after stamping can be computed in principle for arbitrary die shape using computer aided flow simulations. However, in practice it is relatively simple to determine the shapes, and to optimize the various dimensions to obtain the desired shapes through limited experimentation now that the basic principles behind the process set forth herein are understood. For example, the diameter of the nozzle 30, and the width W and thickness T of the billet can be varied in a systematic manner to achieve the desired vein shape and dimensions. Such optimization is routine in bar soap manufacturing and is well within the capabilities of artisans in this field.

EXAMPLES

The following examples illustrate various aspects of the invention as well as preferred embodiments.

Example 1

The compositions of the outer surfactant phase and the inner thermoplastic phases used to prepare the bars of example 1 are shown in Table 1

TABLE 1

Compositions used to prepare the bars of Example 1

| INGREDIENT | OUTER PHASE Wt % | INNER PHASE Wt % |
|---|---|---|
| Soap | 71 | 70 |
| Sunflower oil | | 2 |
| Glycerine | 4 | |
| Propylenoglycol | 1.5 | |
| Triethanolamine | 1.5 | |
| Sorbitol | 6 | |
| Coconut fatty Acid | 1.25 | 0.5 |
| Sodium cocoyl isethionate/stearic acid blend (about 3:1) | | 15 |
| Water | 13.5 | 11 |
| Minors (preservatives pigments, dyes) | 0.25 | 0.5 |
| Perfume | 1 | 1 |

Billets were formed by coextrusion according to the BAR MANUFACTURING PROCESS described above. In summary, the outer phase composition was prepared by combining soap noodles (85/15 Tallow/coco soap—sodium salt) with the remaining ingredients in Table 1 in a Z-blade mixer and passing the mixture through a 3-roll mill. The inner phase composition was also prepared in a Z-blade mixer. In this case noodles comprising acyl isethionate (prepared by direct esterification) and stearic acid where combined with the remaining ingredients in Table 1. The inner phase mixture was also passed through a 3-roll mill.

The outer and inner phase compositions were added to the respective hoppers of two extruders, and the extrudates were fed to the injector assembly (FIG. 3). The coextrusion was carried out at a temperature of 35° C. at an extrusion rate of 1.5 kg/min through an eyeplate having a 3.5×3.5 cm cross section to form billets cut to about 7 cm in lengths.

In this example the aperture 30 (FIG. 3) was circular in cross section having a radius of about 0.5 to 1.5 cm. The properties of the composite billets are described in Table 2

The billets were stamped with a die set (two dies) defining a mold having a volume of 88 $cm^3$ to produce soap bars. The average temperature at which the composite billet was stamped was in the range of about 30° C.-50° C. (e.g., 35 to 45° C.).

Each bar had an overall dimension of approximately 8×5.5 cm. The upper half had a portion of the top surface which was flat which was approximately 4.5×2.6 cm. This plat portion joined the medial edge line via downwardly curved surfaces. The bottom half of the bar was saddle shaped.

Each bar contained an inner vein located in a slice approximately centered at the medial X,Y plane of the bar defined by the parting line of the mold. When viewed through the top surface of the bar perpendicular to the flat portion of the top face, a pink-opal vein was clearly visible, had curved lateral edges and occupied about 70% of the area of the bar in the medial X,Y plane. The vein did not extend to the lateral edge line of the bar and the flashing that was formed during stamping was predominantly composed of the outer phase.

TABLE 2

Properties of composite billet used to make the bars of Example 1

| | |
|---|---|
| BILLET GEOMETRY | |
| Length (L - cm) | 7.2-7.5 |
| Width (W - cm) | 3.5 |
| Thickness (T - cm) | 3.5 |
| Overall average volume (outer + inner phases - $cm^3$) | 97.2 |
| INNER PHASE | See Table 1 for composition |
| Geometrical form and dimensions | Right Circular Cylinder<br>Length ~7.1 cm<br>Radius 0.35 to 0.5 cm |
| Location | Cylinder centered in billet cross section |
| Hardness ($lb/in^2$) | 33.5 $lb/in^2$ @ 45° C. |
| Color | Pink<br>Opal |
| OUTER PHASE | See Table 1 for composition |
| Appearance | Translucent, pale yellow to light amber |
| Hardness ($lb/in^2$) | 40 $lb/in^2$ @ 45° C. |

Example 2

The compositions of the outer surfactant phase and the inner thermoplastic phases that were used to prepare the bars of example 2 are shown in Table 3. In this case both the inner and outer compositions were based on soap as the surfactant.

TABLE 3

Compositions used to prepare the bars of Example 2

| INGREDIENT | OUTER PHASE Wt % | INNER PHASE Wt % |
|---|---|---|
| Soap | 71 | 71.75 |
| Sunflower oil | | 2 |
| Glycerine | 4 | 1 |
| Propylenoglycol | 1.5 | |
| Triethanolamine | 1.5 | |
| Sorbitol | 6 | |
| Coco Fatty Acid | 1.25 | |
| Water | 13.5 | 13.5 |
| Minors (preservatives pigments, dyes) | 0.25 | 0.5 |
| Perfume | 1 | 1 |

Billets were formed by the coextrusion process described in Example 1. The properties of the composite billet are described in Table 4.

The billets were stamped with a die set (two dies) defining a mold having a volume of about 88 $cm^3$ to produce soap bars. The average temperature at which the composite billet was stamped was in the range of about 30° C.-50° C. (e.g., 35 to 45° C.).

The top surface of the bars of example 2 had a different shape from the bars of Example 1. Each bar was 7.6 cm long×5.5 cm wide. A portion of the top surface of the bar was flat (4.5×2.6 cm). This flat top portion joined the meridian edge (parting line) through a curvilinear band of about 3.5 cm positioned diagonally on the top surface. The bottom surface of the bar was saddle shaped similar to bars of Example 1.

Each bar contained an inner vein located in a slice approximately centered at the medial X, Y plane of the bar. When viewed through the top surface of the bar perpendicular to the flat portion of the top face, a white vein was clearly visible through the translucent outer phase. This vein had curved lateral edges and occupied about 80% of the area of the bar in the medial X, Y plane. The thickness of the vein varied along its expanse and was in a range of about 0.2-0.4 cm. The vein was about 4.5 cm at its widest point and 2.5 cm at its narrowest point. The width to thickness ratio thus fell between about 6 and about 22. The vein did not extend to the lateral edge line of the bar and the flashing that was formed during stamping was primarily composed of the outer phase. During use the vein remained distinctive. After about 70-80% of the mass of the bar was worn away during use only the vein remained which provided continued lather.

TABLE 4

Properties of composite billet used to make the bars of Example 2

| | |
|---|---|
| BILLET GEOMETRY | |
| Length (L - cm) | 7.2-7.5 |
| Width (W - cm) | 3.5 |
| Thickness (T - cm) | 3.5 |
| Overall average volume (outer + inner phases - $cm^3$) | 97.2 |
| INNER PHASE | See Table 2 for composition |
| Geometrical form and dimensions | Right Circular Cylinder |
| | Length ~7.1 cm |
| | Radius 0.35 to 0.5 cm |
| Location | Cylinder centered in billet cross section |
| Hardness ($lb/in^2$) | 28 $lb/in^2$ @ 40° C. |
| Color | white |
| OUTER PHASE | See Table 2 for composition |
| Appearance | Translucent, pale yellow to light amber |
| Hardness ($lb/in^2$) | 43.5 $lb/in^2$ @ 40° C. |

Example 3

The compositions of the outer surfactant phase and the inner thermoplastic phases used to prepare the bars of example 3 are shown in Table 5

TABLE 5

Compositions used to prepare the bars of Example 3

| INGREDIENT | OUTER PHASE Wt % | INNER PHASE Wt % |
|---|---|---|
| Soap | 70.75 | 70 |
| Sunflower oil | | 2 |
| Glycerine | 9 | |
| Propylenoglycol | 1.5 | |
| Triethanolamine | 1.5 | |
| Sorbitol | | |
| Coco Fatty Acid | 1.25 | 0.5 |
| Sodium cocoyl isethionate/stearic acid blend (about 3:1) | | 15 |
| Water | 13.5 | 11 |
| Minors (preservatives pigments, dyes) | 0.5 | 0.5 |
| Perfume | 1 | 1 |
| Hardness ($lb/in^2$) | 43 @ 44° C. | 36@ 44° C. |

Billets are prepared and bars stamped using the same equipment and procedures as set forth in Example 1 except that the diameter of the nozzle 30 is varied (keeping a circular cross section) between about 0.2 and about 3.0 cm in diameter.

The bars so prepared are similar to those described in example 1 except that the width and thickness varies depending upon the diameter of the nozzle. All the bars have translucent outer phases and a pink-opal inner vein. The area occupied by the vein in the horizontal plane varies from less than 10% to 100% of maximum horizontal area of the bar. It is found that for small diameter nozzles (e.g., less than about 0.3 cm in diameter) the inner vein occupies less than about 15% of the horizontal area and gives an appearance more like a central stripe rather than a distinctive ribbon-like vein. In contrast with larger diameter nozzles (about 0.8 cm and above) a significant portion of the inner phase exuded from the mold during stamping.

Example 4

The compositions of the inner and outer phases were identical to that used in Example 1 except that a white pigment, $TiO_2$, was incorporated in the outer phase composition to make it opaque.

Billets were prepared and bars stamped using the same equipment and procedures as set forth in Example 1. The bars so prepared were similar to those described in Example 1 except that the outer phase was opaque. In this case, the vein was not visible until a significant portion of the bar was worn away. The cross sectional shapes of nozzle 30 the thickness to width ratio can be varied to alter the extent of wear required to expose the vein phase.

Example 5

Nozzles having different cross-sections shown in Table 6 are used to prepare composite billets utilizing any of the compositions in the forgoing examples. The inner veins have somewhat different appearance with elliptical and tear drop nozzles providing a gradient of color that is most dense along its central axis.

TABLE 6

Nozzle shapes used to form the billets of Example 5

| | EXAMPLE 5A | EXAMPLE 5B | EXAMPLE 5C |
|---|---|---|---|
| Nozzle cross-section | Rectangle | Ellipse | Tear drop |
| Dimensions | W: 1 cm | D1: 1.2 cm | W: 1 cm |
| | T: 0.2 cm | D2: 0.4 cm | Tm: 0.3 |

The invention claimed is:

1. A process for the manufacture of a soap bar comprising an artisan crafted appearance, said process comprising the steps of:

i) injecting a thermoplastic mass into an extruded soap mass comprises 25-95% surfactant undergoing substantially plug flow, said injection being directed parallel with the flow of the extruded soap so as to form a composite mass comprising an outer extruded soap and an inner thermoplastic mass in the form of a cylinder, wherein the injected thermoplastic mass and the extruded soap mass are thermoplastic over a temperature range of 30° C. to 50° C., and wherein the injected thermoplastic mass has at least some difference in chemical composition from the extruded soap mass, ii) cutting the composite mass into billets, iii) stamping the billet with a set of dies which when joined define a mold, wherein the stamping is in a direction perpendicular to the flow of the extruded soap so as to form a stamped bar having a top and bottom stamped surface bounded by a parting line or edge band and a horizontal plane intersecting the parting line or edge band;

wherein the thickness of the billet is sufficiently larger than the thickness of the mold such that the cylinder comprised of the thermoplastic mass spreads out in a direction orthogonal to the direction of stamping so as to form an inner vein wherein said inner vein is located between the top and bottom stamped faces of the bar and wherein a projection of the inner vein onto the horizontal plane intersecting the parting line or edge band has a maximum width that is at least 20% of a maximum width of the bar in said horizontal plane.

2. The process according to claim 1 wherein the thermoplastic mass comprises one or more surfactants.

3. The process according to claim 1 wherein the extruded soap mass is transparent or translucent.

4. The process according to claim 1 wherein the thermoplastic mass is injected by means of a tube orientated approximately parallel to the direction of the plug flow of extruded soap mass.

5. The process according to claim 1 wherein the thermoplastic mass does not substantially exude from the sides of the die during the stamping step.

6. The process according to claim 1 wherein the stamping step iii) provides a sufficient spreading out of the cylinder having an equivalent cross sectional diameter 2R such that the inner vein so formed has a maximum width Wv, said stamping producing an expansion defined as Wv/2R that is greater than 2.

7. The process according to claim 1 wherein the stamping step iii) provides a sufficient spreading out of the cylinder having an equivalent cross sectional diameter 2R such that the inner vein so formed has a maximum width Wv, said stamping producing an expansion defined as Wv/2R that is greater than 4.

* * * * *